(12) United States Patent
Amin et al.

(10) Patent No.: US 12,220,510 B2
(45) Date of Patent: Feb. 11, 2025

(54) IMPLANTABLE DEVICE FOR TREATING HYPERVOLEMIA

(71) Applicant: Bard Peripheral Vascular, Inc., Franklin Lakes, NJ (US)

(72) Inventors: Murtaza Y. Amin, Farmington, UT (US); Kevin Wessman, Saratoga Springs, UT (US)

(73) Assignee: Bard Peripheral Vascular, Inc., Franklin Lakes, NJ (US)

( * ) Notice: Subject to any disclaimer, the term of this patent is extended or adjusted under 35 U.S.C. 154(b) by 785 days.

(21) Appl. No.: 17/287,100

(22) PCT Filed: Oct. 24, 2019

(86) PCT No.: PCT/US2019/057880
§ 371 (c)(1),
(2) Date: Apr. 20, 2021

(87) PCT Pub. No.: WO2020/086859
PCT Pub. Date: Apr. 30, 2020

(65) Prior Publication Data
US 2021/0393865 A1  Dec. 23, 2021

Related U.S. Application Data

(60) Provisional application No. 62/750,138, filed on Oct. 24, 2018.

(51) Int. Cl.
*A61M 1/28* (2006.01)
*A61M 1/16* (2006.01)
(Continued)

(52) U.S. Cl.
CPC ............ *A61M 1/28* (2013.01); *A61M 1/1623* (2014.02); *A61M 1/267* (2014.02);
(Continued)

(58) Field of Classification Search
CPC ...... A61M 1/28; A61M 1/1623; A61M 1/267; A61M 27/002; A61M 2039/2433;
(Continued)

(56) References Cited

U.S. PATENT DOCUMENTS

| 4,657,530 A | 4/1987 | Buchwald et al. |
| 4,725,207 A | 2/1988 | Buchwald et al. |

(Continued)

FOREIGN PATENT DOCUMENTS

| WO | 13122580 A1 | 8/2013 |
| WO | 18211500 A1 | 11/2018 |
| WO | 18224351 A1 | 12/2018 |

OTHER PUBLICATIONS

PCT/US2019/057880 filed Oct. 24, 2019 International Search Report and Written Opinion dated Feb. 5, 2020.

*Primary Examiner* — Susan S Su
*Assistant Examiner* — Erin A Kim
(74) *Attorney, Agent, or Firm* — Rutan & Tucker LLP (57) ABSTRACT

An implantable device for treating hypervolemia includes an expandable chamber, a rigid chamber coupled to the expandable chamber, a first valve in fluid communication with both the expandable chamber and the rigid chamber, a second valve in fluid communication with the rigid chamber and an exterior of the implantable device, and an osmotic fluid. The expandable chamber includes a first semipermeable membrane. The rigid chamber includes a piston. The first valve has an open position to permit fluid flow between the expandable chamber and the rigid chamber. The second valve has an open position to permit fluid flow from the rigid chamber to the exterior of the implantable device. The osmotic fluid has a higher osmotic concentration than bodily fluid. The osmotic fluid is designed to absorb water from the bodily fluid through the first semipermeable membrane.

23 Claims, 7 Drawing Sheets

(51) Int. Cl.
*A61M 1/26* (2006.01)
*A61M 27/00* (2006.01)
*A61M 39/24* (2006.01)

(52) U.S. Cl.
CPC ... *A61M 27/002* (2013.01); *A61M 2039/2433* (2013.01); *A61M 2205/8243* (2013.01); *A61M 2210/1017* (2013.01); *A61M 2210/1078* (2013.01)

(58) Field of Classification Search
CPC .. A61M 2205/8243; A61M 2210/1017; A61M 2210/107
See application file for complete search history.

(56) References Cited

U.S. PATENT DOCUMENTS

| | | |
|---|---|---|
| 5,037,385 A | 8/1991 | O'Byrne |
| 5,902,336 A | 5/1999 | Mishkin |
| 8,211,053 B2 | 7/2012 | Herbert |
| 8,641,659 B2 | 2/2014 | Soykan et al. |
| 8,876,850 B1 | 11/2014 | Vollmers et al. |
| 9,039,646 B2 | 5/2015 | Lande |
| 9,138,521 B2 | 9/2015 | Solomon et al. |
| 9,138,523 B2 | 9/2015 | Burnett et al. |
| 9,295,764 B2 | 3/2016 | Christensen et al. |
| 9,393,387 B1 | 7/2016 | Mayse et al. |
| 9,656,049 B1 | 5/2017 | Khan et al. |
| 9,675,327 B2 | 6/2017 | Johnson et al. |
| 9,913,968 B2 | 3/2018 | Burnett |
| 9,919,138 B2 | 3/2018 | Lenihan et al. |
| 9,956,336 B2 | 5/2018 | Degen et al. |
| 2004/0049288 A1* | 3/2004 | Levin .................. A61M 1/1678 623/23.65 |
| 2004/0147871 A1* | 7/2004 | Burnett .................. A61M 39/24 604/9 |
| 2009/0234266 A1 | 9/2009 | Solomon et al. |
| 2009/0287178 A1* | 11/2009 | Herbert ............... A61M 27/002 604/500 |
| 2010/0312163 A1 | 12/2010 | Forsell |
| 2012/0220926 A1 | 8/2012 | Soykan et al. |
| 2014/0012180 A1 | 1/2014 | Levin et al. |
| 2015/0343186 A1 | 12/2015 | Nitzan et al. |
| 2017/0128654 A1 | 5/2017 | Feld |
| 2018/0056050 A1 | 3/2018 | Degen et al. |
| 2018/0060520 A1 | 3/2018 | Degen et al. |
| 2018/0229015 A1 | 8/2018 | Pisano et al. |
| 2018/0344917 A1 | 12/2018 | Inhaber et al. |

* cited by examiner

IMPLANTABLE DEVICE FOR TREATING HYPERVOLEMIA

PRIORITY

This application is a U.S. national stage application from International Application No. PCT/US2019/057880, filed Oct. 24, 2019, which claims the benefit of priority to U.S. Provisional Patent Application No. 62/750,138, filed Oct. 24, 2018, each of which is incorporated by reference in its entirety into this application.

BACKGROUND

Hypervolemia, or fluid overload, is a medical condition in which the volume of blood in the intravascular compartment is in excess of normal as a result of plasma retaining too much water. Water can accumulate in patients suffering from chronic kidney disease, particularly in advanced stages thereof such as end-stage renal disease ("ESRD"), where the kidneys are no longer effective in filtering out water in excess of that the body needs. Water can also accumulate in patients suffering from chronic heart disease such as congestive heart failure ("CHF"), where the heart is no longer effective in pumping the blood to the kidneys to filter out the water in excess of that the body needs. The volume of blood in the intravascular compartment in excess of normal can lead to fluid buildup in the peritoneal and pleural cavities causing shortness of breath, which can degrade quality of life. The volume of blood in the intravascular compartment in excess of normal can also lead to hypertension and stress on the heart, which can exacerbate other diseases such as CHF leading to death. Therefore, managing hypervolemia is important to those suffering from the medical condition. Disclosed herein is an implantable device and methods thereof that address the foregoing.

SUMMARY

Disclosed herein is an implantable device for treating hypervolemia including, in some embodiments, an expandable chamber, a rigid chamber coupled to the expandable chamber, a first valve in fluid communication with both the expandable chamber and the rigid chamber, a second valve in fluid communication with the rigid chamber and an exterior of the implantable device, and an osmotic fluid. The expandable chamber includes a first semipermeable membrane. The rigid chamber includes a piston. The first valve has an open position to permit fluid flow between the expandable chamber and the rigid chamber. The second valve has an open position to permit fluid flow from the rigid chamber to the exterior of the implantable device. The osmotic fluid has a higher osmotic concentration than bodily fluid. The osmotic fluid is designed to absorb water from the bodily fluid through the first semipermeable membrane.

In some embodiments, the implantable device further includes a pump. The pump is designed to move any fluid contents of the implantable device through the first valve in the open position or the second valve in the open position.

In some embodiments, the piston is configured to perform a pump-actuated pull stroke in the rigid chamber when the first valve is in the open position to pull any fluid contents of the expandable chamber into the rigid chamber.

In some embodiments, the piston is configured to perform a pump-actuated push stroke in the rigid chamber when the second valve is in the open position to push any fluid contents in the rigid chamber and expel permeate from the implantable device.

In some embodiments, at least one of the first semipermeable membrane or the second semipermeable membrane is a dialysis membrane.

In some embodiments, the osmotic fluid is an aqueous solution of a dissolved polymer.

In some embodiments, the first semipermeable membrane and the second semipermeable membrane are designed to prevent the aqueous solution of the dissolved polymer from passing through.

In some embodiments, the implantable device is configured for implantation in a peritoneal cavity of a patient.

In some embodiments, the implantable device is shunted to a ureter of the patient for elimination of excess water through the bladder.

In some embodiments, the implantable device further includes an inductive coil configured to couple with a complementary inductive coil of a companion device, wherein the companion device is operable to couple with mains electricity to charge or power the implantable device by induction.

Also disclosed herein is an implantable device for treating hypervolemia including, in some embodiments, an expandable chamber, a rigid chamber including a piston, a first valve between the expandable chamber and the rigid chamber, a second valve between the rigid chamber and an exterior of the rigid chamber, and a fluid within the implantable device. The expandable chamber includes a first semipermeable membrane over at least a portion of the expandable chamber. The expandable chamber is configured to expand when the fluid is disposed in the expandable chamber and osmotically absorb water through the first semipermeable membrane from a bodily fluid outside the expandable chamber having a lower osmotic concentration. The first valve between the expandable chamber and the rigid chamber is configured to allow the fluid to flow between the expandable chamber and the rigid chamber when the first valve is open. The second valve between the rigid chamber and the exterior of the rigid chamber is configured to allow the fluid to flow from the rigid chamber into a second semipermeable membrane to expel the water from the implantable device when the second valve is open.

In some embodiments, the implantable device further includes a pump. The pump is configured to operate in concert with both the first valve and the second valve. The pump is configured to move the fluid between the expandable chamber and the rigid chamber when the first valve is open, and the pump is configured to move the fluid from the rigid chamber to the second semipermeable membrane when the second valve is open.

In some embodiments, the piston is configured to perform a pump-actuated pull stroke in the rigid chamber when the first valve is open to pull the fluid from the expandable chamber into the rigid chamber.

In some embodiments, the piston is configured to perform a pump-actuated push stroke in the rigid chamber when the second valve is open to push the fluid from the rigid chamber through the second semipermeable membrane to expel the water from the implantable device.

In some embodiments, the first semipermeable membrane, the second semipermeable membrane, or both the semipermeable membranes are dialysis membranes.

In some embodiments, the fluid within the implantable device is an aqueous solution of a dissolved polymer.

In some embodiments, the fluid within the implantable device is an aqueous solution of a dissolved polymer excluded from passing through the first and second semipermeable membranes.

In some embodiments, the implantable device is configured for implantation in a peritoneal cavity of a patient to remove water in excess of that the patient needs.

In some embodiments, the implantable device is shunted to a ureter of the patient for elimination of the water in excess of that the patient needs through the bladder.

In some embodiments, the implantable device further includes an inductive coil configured to couple with a complementary inductive coil of a companion device operable to couple with mains electricity to charge or power the implantable device by induction.

Also disclosed herein is an implantable device for treating hypervolemia including, in some embodiments, a first expandable chamber, a second expandable chamber, a rigid chamber including a piston, a number of valves, and a fluid within the implantable device. The first expandable chamber includes a first semipermeable membrane over at least a portion of the first expandable chamber. The second expandable chamber includes a second semipermeable membrane over at least a portion of the second expandable chamber. Each expandable chamber of the first and second expandable chambers is configured to expand when the fluid is disposed therein and osmotically absorb water from a bodily fluid outside the implantable device having a lower osmotic concentration. The number of valves includes a first valve between the first expandable chamber and the rigid chamber and a second valve between the second expandable chamber and the rigid chamber. Each valve of the first and second valves is configured to allow the fluid to flow between adjacent chambers when the valve is open. The number of valves also includes a third valve between the rigid chamber and an exterior of the rigid chamber and a fourth valve between the rigid chamber and the exterior of the rigid chamber, wherein the third valve and the fourth valve are separated from each other by the piston. The third valve is configured to allow the fluid to flow from the rigid chamber into a third semipermeable membrane to expel the water from the implantable device when the third valve is open. The fourth valve is configured to allow the fluid to flow from the rigid chamber into a fourth semipermeable membrane to expel the water from the implantable device when the fourth valve is open.

In some embodiments, the implantable device further includes a pump. The pump is configured to operate in concert with the number of valves. The pump is configured to move the fluid between the first expandable chamber and the rigid chamber when the first valve is open while also moving the fluid from the rigid chamber to the fourth semipermeable membrane when the fourth valve is open. The pump is also configured to move the fluid between the second expandable chamber and the rigid chamber when the second valve is open while also moving the fluid from the rigid chamber to the third semipermeable membrane when the third valve is open.

In some embodiments, the piston is configured to perform a pump-actuated pull stroke in the rigid chamber when the first and fourth valves are open to simultaneously pull the fluid from the first expandable chamber into the rigid chamber and push the fluid from the rigid chamber through the fourth semipermeable membrane to expel the water from the implantable device.

In some embodiments, the piston is configured to perform a pump-actuated push stroke in the rigid chamber when the second and third valves are open to simultaneously push the fluid from the rigid chamber through the third semipermeable membrane to expel the water from the implantable device and pull the fluid from the second expandable chamber into the rigid chamber.

In some embodiments, each semipermeable membrane of the first, second, third, and fourth semipermeable membranes is a dialysis membranes.

In some embodiments, the fluid within the implantable device is an aqueous solution of a dissolved polymer.

In some embodiments, the fluid within the implantable device is an aqueous solution of a dissolved polymer excluded from passing through the first, second, third, and fourth semipermeable membranes.

In some embodiments, the implantable device is configured for implantation in a peritoneal cavity of a patient to remove water in excess of that the patient needs.

In some embodiments, the implantable device is shunted to a ureter of the patient for elimination of the water in excess of that the patient needs through the bladder.

In some embodiments, the implantable device further includes an inductive coil configured to couple with a complementary inductive coil of a companion device operable to couple with mains electricity to charge or power the implantable device by induction.

Also disclosed herein is a method for treating hypervolemia with the foregoing implantable device(s), the method comprising one or more functions described herein associated with the implantable device(s) for treating hypervolemia.

These and other features of the concepts provided herein will become more apparent to those of skill in the art in view of the accompanying drawings and following description, which disclose particular embodiments of such concepts in greater detail.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "front," "back," "top," "bottom," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

Unless defined otherwise, all technical and scientific terms used herein have the same meaning as commonly understood by those of ordinary skill in the art.

As set forth above, hypervolemia, or fluid overload, is a medical condition in which the volume of blood in the intravascular compartment is in excess of normal as a result of plasma retaining too much water. Water can accumulate in patients suffering from chronic kidney disease, particularly in advanced stages thereof such as end-stage renal disease ("ESRD"), where the kidneys are no longer effective in filtering out water in excess of that the body needs. Water can also accumulate in patients suffering from chronic heart disease such as congestive heart failure ("CHF"), where the heart is no longer effective in pumping the blood to the kidneys to filter out the water in excess of that the body needs. The volume of blood in the intravascular compartment in excess of normal can lead to fluid buildup in the peritoneal and pleural cavities causing shortness of breath, which can degrade quality of life. The volume of blood in the intravascular compartment in excess of normal can also lead to hypertension and stress on the heart, which can exacerbate other diseases such as CHF leading to death. Therefore, managing hypervolemia is important to those suffering from the medical condition. Disclosed herein is an implantable device and methods thereof that address the foregoing.

FIGS. 1A-1F illustrate a device 100 for treating hypervolemia in a number of different stages of operation in accordance with some embodiments.

As shown, the implantable device 100 includes an expandable chamber 110, a rigid chamber 120 including a piston 122, a first valve 132 between the expandable chamber 110 and the rigid chamber 120, a second valve 134 between the rigid chamber 120 and an exterior of the rigid chamber 120, and a fluid 140 within the implantable device 100.

The expandable chamber 110 includes a first semipermeable membrane 112 over at least a portion of the expandable chamber 110. The expandable chamber 110 is configured to expand when the fluid 140 is disposed in the expandable chamber 110 and osmotically absorb water into the fluid 140 through the first semipermeable membrane 112 from a bodily fluid outside the expandable chamber 110 having a lower osmotic concentration than the fluid 140. (See FIGS. 1A and 1B.)

The first valve 132 between the expandable chamber 110 and the rigid chamber 120 is configured with an open position to allow or permit the fluid 140 to flow between the expandable chamber 110 and the rigid chamber 120 when the first valve 132 is open or in the open position. (See FIGS. 1B and 1C.)

The second valve 134 between the rigid chamber 120 and the exterior of the rigid chamber 120 is configured with an open position to allow or permit the fluid 140 to flow from the rigid chamber 120 into a second semipermeable membrane 124 to expel the water from the implantable device 100 when the second valve 134 is open or in the open position. (See FIGS. 1D and 1E.)

The implantable device 100 further includes a pump (not shown) such as a gear-driven piston pump to move any fluid contents of the implantable device through the implantable device 100 (e.g., through the first valve 132 or the second valve 134 when in the opened position). The pump is configured to operate in concert with both the first valve 132 and the second valve 134. The pump is configured to move the fluid 140 between the expandable chamber 110 and the rigid chamber 120 when the first valve 132 is open. The pump is also configured to move the fluid 140 from the rigid chamber 120 to the second semipermeable membrane 124 when the second valve 134 is open.

The piston 122 is configured to perform a pump-actuated pull stroke in the rigid chamber 120 when the first valve 132 is open to pull any fluid contents such as the fluid 140 from the expandable chamber 110 into the rigid chamber 120. The piston 122 is also configured to perform a pump-actuated push stroke in the rigid chamber 120 when the second valve 134 is open to push any fluid contents such as the fluid 140 from the rigid chamber 120 through the second semipermeable membrane 124 to expel the water (as permeate) from the implantable device 100, thereby producing a retentate of the fluid 140. Upon closing the second valve 134, or returning the second valve to a closed position, and opening the first valve 132, or returning the first valve 132 to the open position, the pump-actuated push stroke can be further utilized to push the retentate of the fluid 140 from the rigid chamber 120 into the expandable chamber 110 for another cycle.

In addition to the foregoing, the pump-actuated strokes can be utilized in a cycling mode of operation of the implantable device 100, in which the fluid 140 is cycled back and forth between the expandable chamber 110 and the rigid chamber 120 through the first valve 132 when in the open position. The cycling mode of operation ensures the fluid 140 is mixed such that the osmotic concentration of the fluid 140 near an inside surface of semipermeable membrane 124 remains high enough for osmosis through the semipermeable membrane 124. Depending upon the activity level of the patient in which the implantable device 100 is implanted the cycling mode of operation of the implantable device 100 might not be necessary. That is, the activity level of the patient might be enough to mix the fluid 140 to maintain a high enough osmotic concentration of the fluid 140 near the inside surface of semipermeable membrane 124 for water osmosis through the semipermeable membrane 124.

Figure 1A:
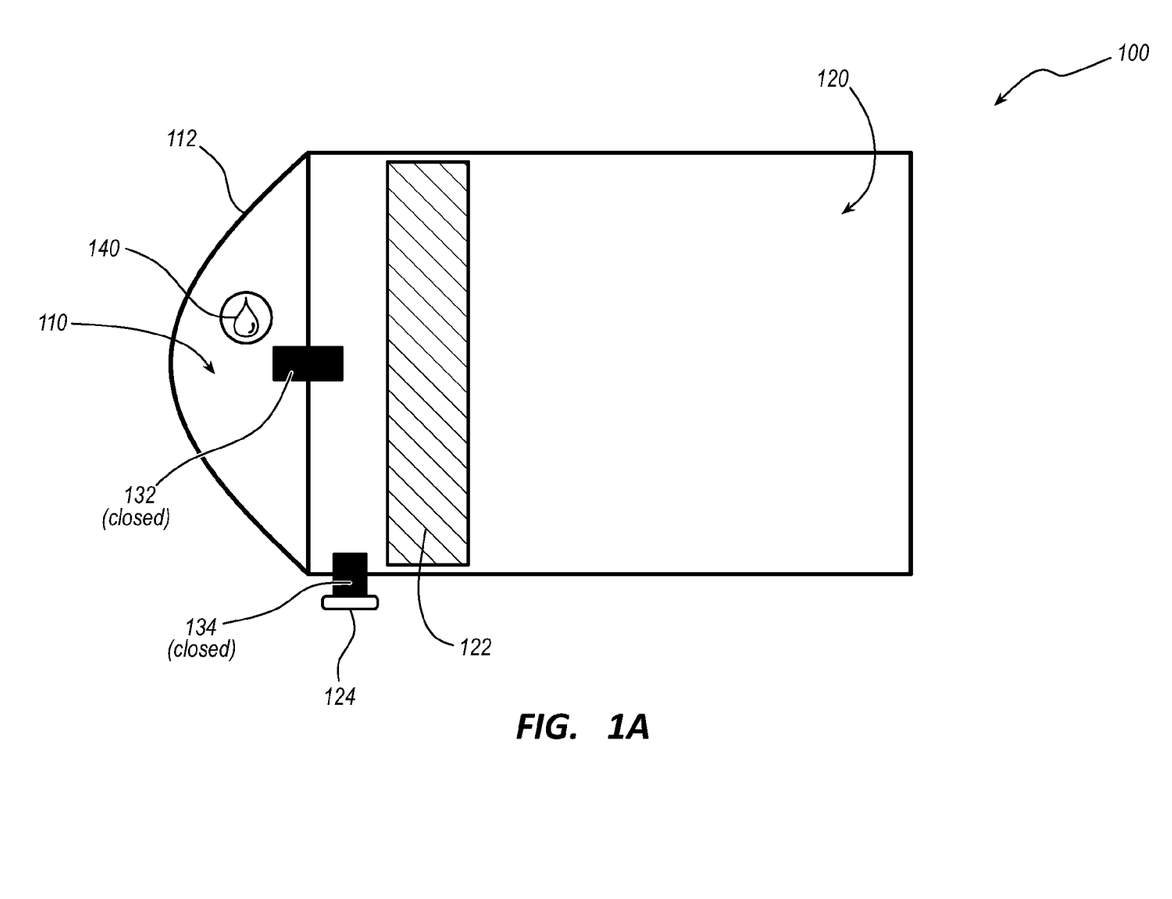
FIG. 1A illustrates a device for treating hypervolemia in a first stage of operation in accordance with some embodiments.
Figure 1B:
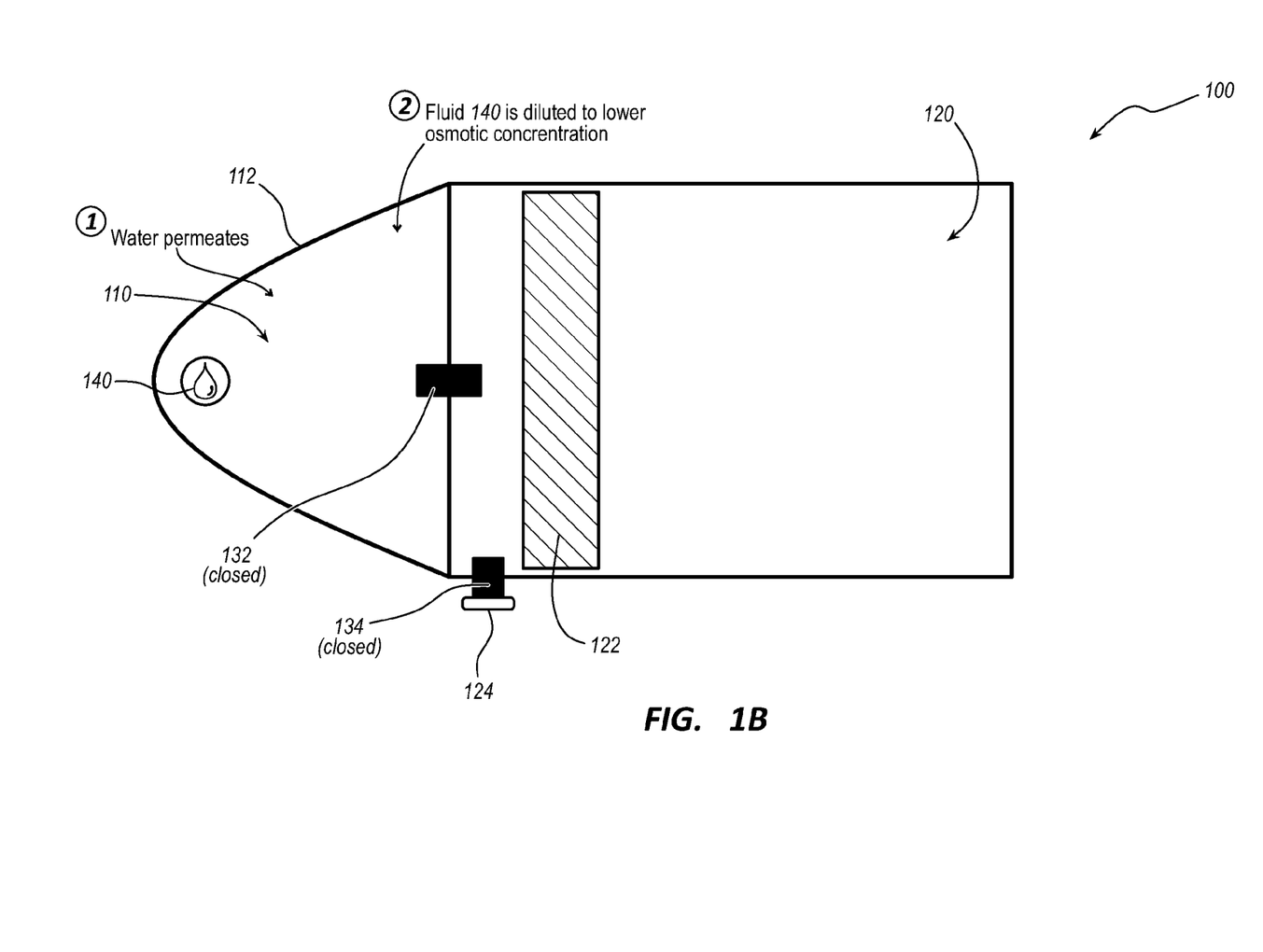
FIG. 1B illustrates a device for treating hypervolemia in a second stage of operation in accordance with some embodiments.
Figure 1C:
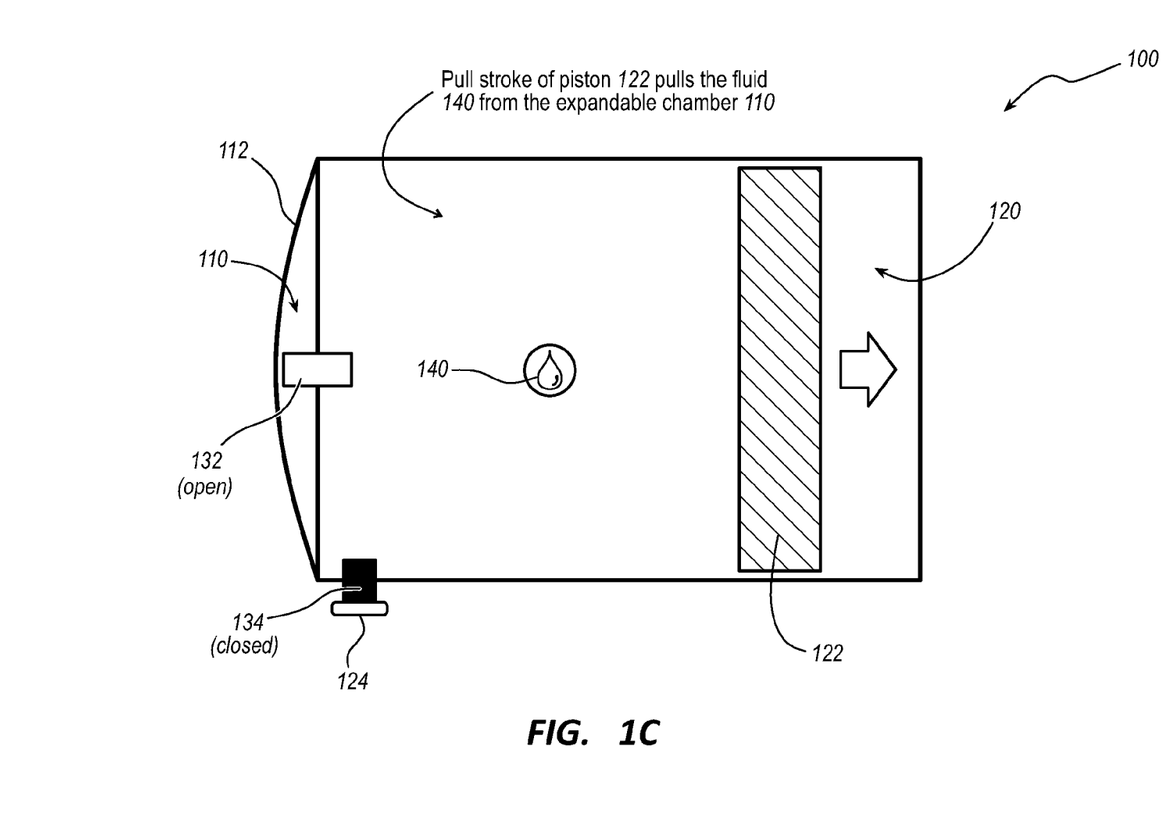
FIG. 1C illustrates a device for treating hypervolemia in a third stage of operation in accordance with some embodiments.
Figure 1D:
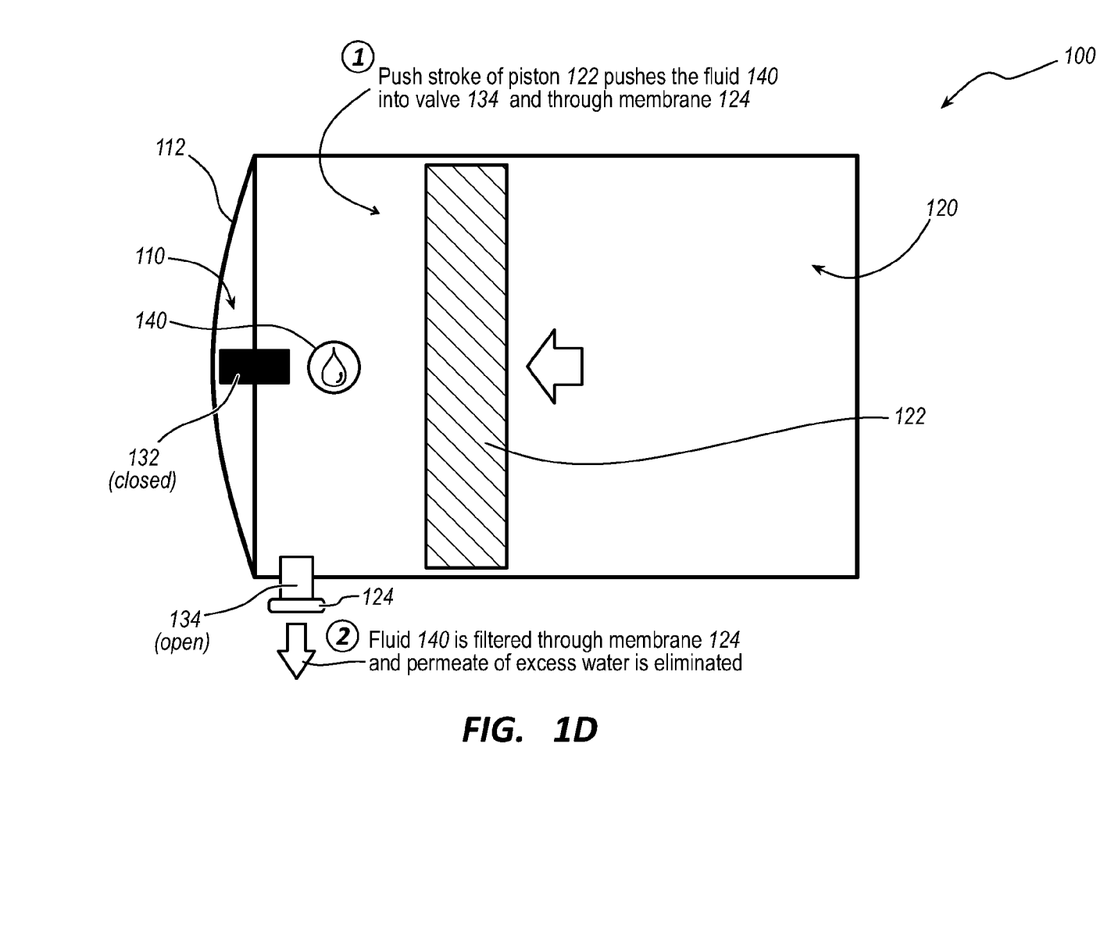
FIG. 1D illustrates a device for treating hypervolemia in a fourth stage of operation in accordance with some embodiments.
Figure 1E:
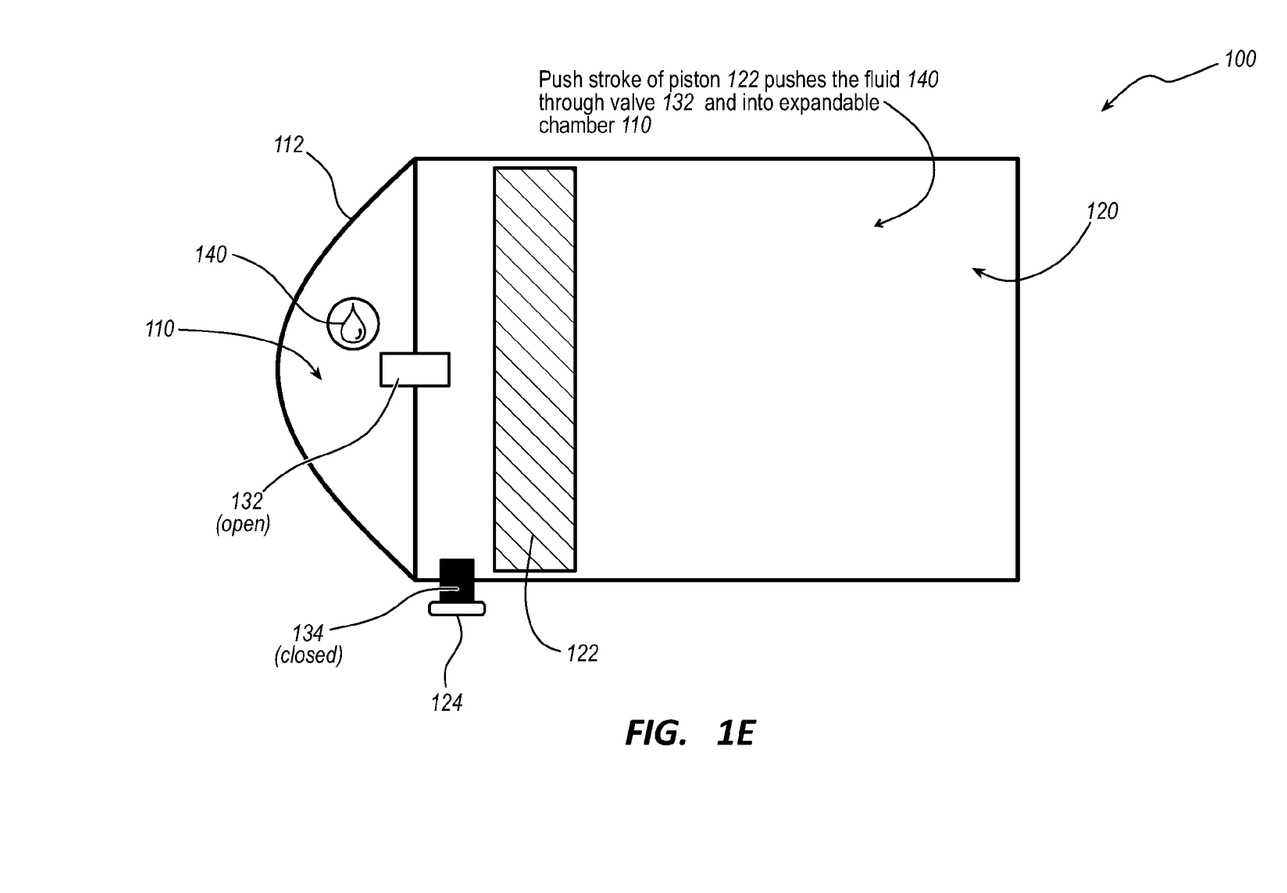
FIG. 1E illustrates a device for treating hypervolemia in a fifth stage of operation in accordance with some embodiments.
Figure 1F:
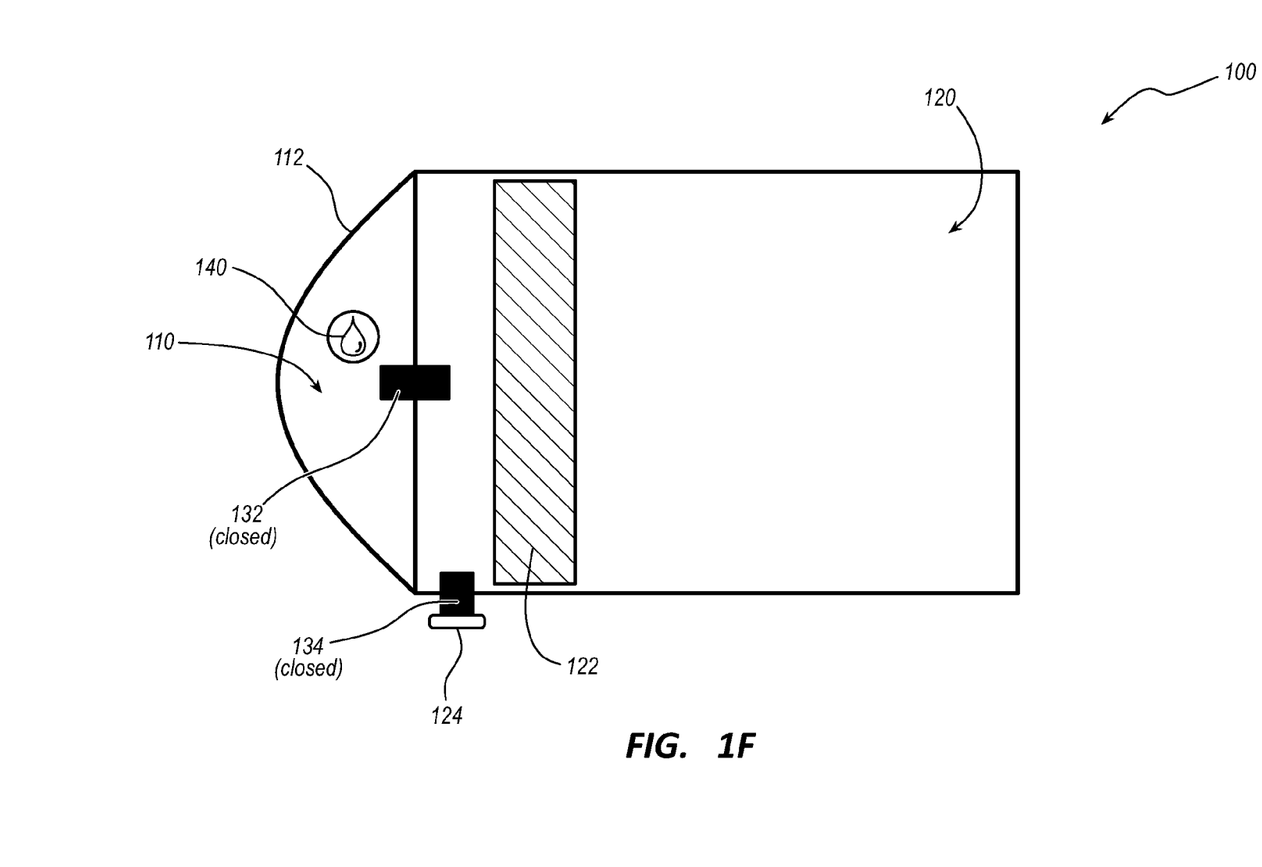
FIG. 1F illustrates a device for treating hypervolemia in a sixth stage of operation in accordance with some embodiments.
Figure 2:
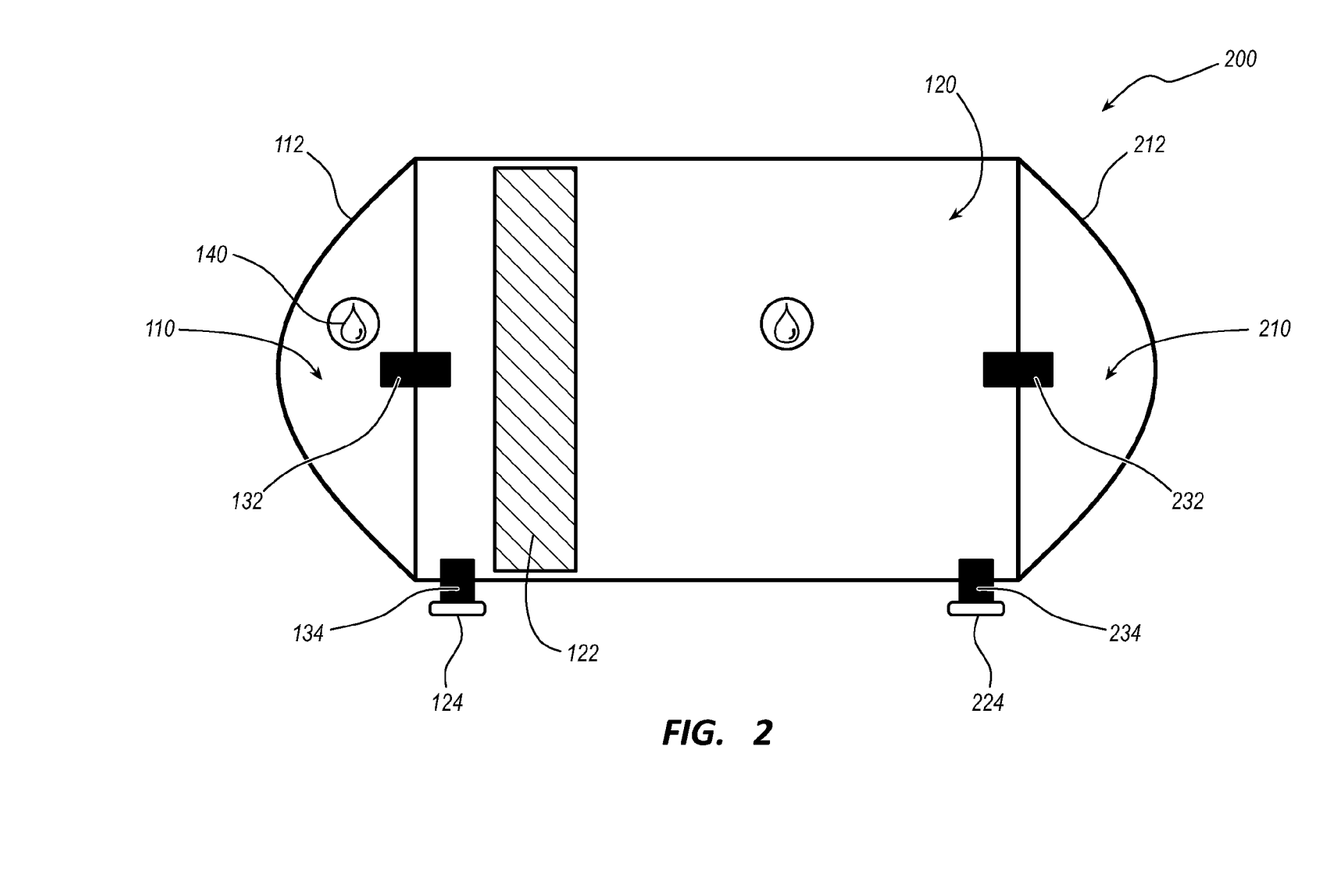
FIG. 2 illustrates another device for treating hypervolemia in accordance with some embodiments.

FIG. 2 illustrates another device 200 for treating hypervolemia in accordance with some embodiments.

As shown, the implantable device 200 includes the first expandable chamber 110, a second expandable chamber 210, the rigid chamber 120 including the piston 122, a number of valves 132, 134, 232, 234, and the fluid 140 within the implantable device 200.

The first expandable chamber 110 includes the first semipermeable membrane 112 over at least a portion of the first expandable chamber 110 as described in reference to the implantable device 100. Likewise, the additional second expandable chamber 210 includes a second semipermeable membrane 212 over at least a portion of the second expandable chamber 210. Each expandable chamber of the first and second expandable chambers 110, 210 is configured to expand when the fluid 140 is disposed therein and osmotically absorbs water from a bodily fluid outside the implantable device 200. That is, the expandable chamber 110 expands when the fluid 140 in the expandable chamber 110 osmotically absorbs water into the fluid 140 through the first semipermeable membrane 112 from the bodily fluid outside the expandable chamber 110 when the bodily fluid has a lower osmotic concentration than the fluid 140, and the expandable chamber 210 expands when the fluid 140 in the expandable chamber 210 osmotically absorbs water into the fluid 140 through the second semipermeable membrane 212 from the bodily fluid outside the expandable chamber 210 when the bodily fluid has a lower osmotic concentration than the fluid 140.

The number of valves includes the first valve 132 between the first expandable chamber 110 and the rigid chamber 120 and a second valve 232 between the second expandable chamber 210 and the rigid chamber 120. Each valve of the first and second valves 132, 232 is configured with an open position to allow or permit the fluid 140 to flow between adjacent chambers when the valve is open or in the open position. That is, the first valve 132 between the expandable chamber 110 and the rigid chamber 120 is configured to allow the fluid 140 to flow between the expandable chamber 110 and the rigid chamber 120 when the first valve 132 is open, and the second valve 232 between the expandable chamber 210 and the rigid chamber 120 is configured to allow the fluid 140 to flow between the expandable chamber 210 and the rigid chamber 220 when the second valve 232 is open. The number of valves also includes a third valve 134 between the rigid chamber 120 and an exterior of the rigid chamber 120 and a fourth valve 234 between the rigid chamber 120 and the exterior of the rigid chamber 120, wherein the third valve 134 and the fourth valve 234 are separated from each other by the piston 122. The third valve 134 is configured with an open position to allow or permit the fluid 140 to flow from the rigid chamber 120 into a third semipermeable membrane 124 to expel the water from the implantable device 200 when the third valve 134 is open or in the open position. The fourth valve 234 is configured with an open position to allow or permit the fluid 140 to flow from the rigid chamber 120 into a fourth semipermeable membrane 224 to expel the water from the implantable device 200 when the fourth valve 234 is open or in the open position.

The implantable device 200 further includes a pump (not shown) as described in reference to the implantable device 100. Likewise, the pump is configured to operate in concert with the number of valves 132, 134, 232, 234. The pump is configured to move the fluid 140 between the first expandable chamber 110 and the rigid chamber 120 when the first valve 123 is open while also moving the fluid 140 from the rigid chamber 120 to the fourth semipermeable membrane 224 when the fourth valve 234 is open. The pump is also configured to move the fluid 140 between the second expandable chamber 210 and the rigid chamber 120 when the second valve 232 is open while also moving the fluid 140 from the rigid chamber 210 to the third semipermeable membrane 124 when the third valve 134 is open.

The piston 122 is configured to perform a pump-actuated pull stroke in the rigid chamber 120 when the first and fourth valves 132, 234 are open to simultaneously pull any fluid contents such as the fluid 140 from the first expandable chamber 110 into the rigid chamber 120 proximate the first expandable chamber 110 and push any fluid contents such as the fluid 140 from the rigid chamber 120 proximate the expandable chamber 210 through the fourth semipermeable membrane 224 to expel the water from the implantable device 200. The piston 122 is also configured to perform a pump-actuated push stroke in the rigid chamber 120 when the second and third 232, 134 valves are open to simultaneously push any fluid contents such as the fluid 140 from the rigid chamber 120 proximate the first expandable chamber 110 through the third semipermeable membrane 124 to expel the water from the implantable device 200 and pull any fluid contents such as the fluid 140 from the second expandable chamber 210 into the rigid chamber 120 proximate the second expandable chamber 210. Like the pump-actuated push stroke described in reference to the implantable device 100, the foregoing pump-actuated strokes can be further utilized with timely opening and closing of the valves to push the retentate of the fluid 140 from the rigid chamber 120 into the expandable chambers 110, 210 for additional cycles. In addition, the foregoing pump-actuated strokes can be further utilized in a cycling mode of operation like that of the implantable device 100.

Each semipermeable membrane of the first, second, third, and fourth semipermeable membranes 112, 124, 212, 224 of the implantable devices 100 and 200 can have pores of a pore size that allows water to permeate through the semipermeable membrane but not larger metabolites such as polypeptides or proteins, cell fragments such as platelets, or cells such as red blood cells or white blood cells. However, the pores of the semipermeable membrane can be sized to allow ions such as $Na^+$, $K^+$, $Ca^{2+}$, $Mg^{2+}$, or $Cl^-$ to permeate through the semipermeable membrane, as well as molecules of lower molecular weight than the foregoing larger metabolites such as urea or creatinine. An example of such a semipermeable membrane includes, but is not limited to, a dialysis membrane.

The fluid 140, or osmotic fluid, within the implantable device 100 or 200 can be an aqueous solution of a dissolved polymer such as poly(ethylene glycol) ("PEG") or sodium polyacrylate, which dissolved polymer is excluded based on size from passing through any semipermeable membrane of the first, second, third, and fourth semipermeable membranes 112, 124, 212, 224. The initial or basal concentration of the dissolved polymer in the fluid 140 is sufficient to create an osmotic potential for removing the water in excess of that the patient needs through the first semipermeable membrane 112 or the second semipermeable membrane 212 while the implanted device 100 or 200 is implanted in the patient. That is, the osmotic fluid has a higher osmotic concentration than bodily fluid, which allows the osmotic fluid to absorb water from the bodily fluid through the first semipermeable membrane 112 or the second semipermeable membrane 212 while the implanted device 100 or 200 is implanted in the patient.

Each implantable device of the implantable device 100 and the implantable device 200 is configured for implantation in at least a peritoneal cavity of a patient to remove water that builds up in the patient's peritoneal cavity (a condition known as ascites) for one or more reasons including hypervolemia or liver disease. The peritoneal cavity is an advantageous location for the implantable device 100, 200 because movement of the patient allows the fluid 140 in the expandable chambers 110, 210 to keep moving fluid around, thereby encouraging movement that maintains a concentration gradient that promotes osmosis. In addition, the implantable device 100 can be shunted to a ureter of the patient for elimination of the water in excess of that the patient needs through the patient's bladder.

Because the implantable devices 100 and 200 are electrically powered devices, each implantable devices of the implantable device 100 and the implantable device 200 further includes an inductive coil (not shown) configured to couple with a complementary inductive coil of a companion device such as a belt operable to couple with mains electricity to charge or power the implantable device by induction. For example, the belt can be plugged in and worn during the day when the patient is resting or at night when the patient is sleeping.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An implantable device for treating hypervolemia, comprising:
   an expandable chamber including a first semipermeable membrane;
   a rigid chamber coupled to the expandable chamber, the rigid chamber including a piston;
   a first valve in fluid communication with both the expandable chamber and the rigid chamber, the first valve having an open position to permit fluid flow from the expandable chamber to the rigid chamber and from the rigid chamber to the expandable chamber;
   a second valve in fluid communication with the rigid chamber and an exterior of the implantable device, the second valve including a second semipermeable membrane, the second valve having an open position to permit fluid flow from the rigid chamber to the exterior of the implantable device; and
   an osmotic fluid having a higher osmotic concentration than bodily fluid, the osmotic fluid designed to absorb water from the bodily fluid through the first semipermeable membrane into the expandable chamber.

2. The implantable device according to claim 1, further comprising a pump, wherein the pump is designed to move any fluid contents of the implantable device through the first valve in the open position or the second valve in the open position.

3. The implantable device according to claim 1, wherein the piston is configured to perform a pump-actuated pull stroke in the rigid chamber when the first valve is in the open position to pull any fluid contents of the expandable chamber into the rigid chamber.

4. The implantable device according to claim 1, wherein the piston is configured to perform a pump-actuated push stroke in the rigid chamber when the second valve is in the open position to push any fluid contents in the rigid chamber and expel permeate from the implantable device.

5. The implantable device according to claim 1, wherein at least one of the first semipermeable membrane or the second semipermeable membrane is a dialysis membrane.

6. The implantable device according to claim 1, wherein the osmotic fluid is an aqueous solution of a dissolved polymer, the first semipermeable membrane and the second semipermeable membrane designed to prevent the aqueous solution of the dissolved polymer from passing through.

7. The implantable device according to claim 1, wherein the implantable device is configured for implantation in a peritoneal cavity of a patient.

8. The implantable device according to claim 7, wherein the implantable device is shunted to a ureter of the patient for elimination of excess water through a bladder of the patient.

9. The implantable device according to claim 1, further comprising an inductive coil configured to couple with a complementary inductive coil of a companion device, the companion device operable to couple with mains electricity to charge or power the implantable device by induction.

10. An implantable device for treating hypervolemia, comprising:
    a first expandable chamber including a first semipermeable membrane;
    a second expandable chamber including a second semipermeable membrane;
    a rigid chamber coupled to each of the first expandable chamber and the second expandable chamber, the rigid chamber including a piston;
    a first valve in fluid communication with both the first expandable chamber and the rigid chamber, the first valve being a two-way valve having an open position to permit fluid flow between the first expandable chamber and the rigid chamber;
    a second valve in fluid communication with both the second expandable chamber and the rigid chamber, the second valve being a two-way valve having an open position to permit fluid flow between the second expandable chamber and the rigid chamber;
    a third valve and a fourth valve in fluid communication with the rigid chamber and an exterior of the implantable device, the third valve including a third semipermeable membrane, the fourth valve including a fourth semipermeable membrane, the third valve and the fourth valve separated by the piston, each of the third valve and the fourth valve having an open position to permit fluid flow from the rigid chamber to the exterior of the implantable device; and
    an osmotic fluid having a higher osmotic concentration than bodily fluid, the osmotic fluid designed to absorb water from the bodily fluid through the first semipermeable membrane into the first expandable chamber and the second semipermeable membrane into the second expandable chamber.

11. The implantable device according to claim 10, further comprising a pump, wherein the pump is designed to move fluid contents of the implantable device through any of the first valve, the second valve, the third valve, and the fourth valve in the open position.

12. The implantable device according to claim 10, wherein the piston is configured to perform a pump-actuated pull stroke in the rigid chamber when the first valve is in the open position to pull fluid contents of the first expandable chamber into the rigid chamber.

13. The implantable device according to claim 12, wherein the piston is configured to simultaneously push the fluid contents from the rigid chamber through the fourth valve in the open position to expel permeate from the implantable device.

14. The implantable device according to claim 10, wherein the piston is configured to perform a pump-actuated pull stroke in the rigid chamber when the second valve is in the open position to pull fluid contents of the second expandable chamber into the rigid chamber.

15. The implantable device according to claim 14, wherein the piston is configured to simultaneously push the fluid contents from the rigid chamber through the third valve in the open position to expel permeate from the implantable device.

16. The implantable device according to claim 10, wherein at least one of the first semipermeable membrane, the second semipermeable membrane, the third semipermeable membrane, and the fourth semipermeable membrane is a dialysis membrane.

17. The implantable device according to claim 10, wherein each of the first semipermeable membrane, the second semipermeable membrane, the third semipermeable membrane, and the fourth semipermeable membrane is a dialysis membrane.

18. The implantable device according to claim 10, wherein the osmotic fluid is an aqueous solution of a dissolved polymer, the first semipermeable membrane, the second semipermeable membrane, the third semipermeable membrane, and the fourth semipermeable membrane designed to prevent the aqueous solution of the dissolved polymer from passing through.

19. The implantable device according to claim 10, wherein the implantable device is configured for implantation in a peritoneal cavity of a patient.

20. The implantable device according to claim 19, wherein the implantable device is shunted to a ureter of the patient for elimination of excess water through a bladder of the patient.

21. The implantable device according to claim 10, further comprising an inductive coil configured to couple with a complementary inductive coil of a companion device, the companion device operable to couple with mains electricity to charge or power the implantable device by induction.

22. The implantable device according to claim 1, wherein the piston is configured to:

perform a pump-actuated pull stroke in the rigid chamber when the first valve is in the open position and the second valve is in a closed position to pull fluid contents of the expandable chamber including absorbed water from the bodily fluid into the rigid chamber through the first valve;

perform a pump-actuated push stroke in the rigid chamber when the first valve is in the closed position and the second valve is in the open position to push any fluid contents in the rigid chamber to expel permeate from the implantable device through the second valve; and continue the pump-actuated push stroke in the rigid chamber when the first valve is in the open position and the second valve is in the closed position to continue to push any fluid contents in the rigid chamber including retentate into the expandable chamber through the first valve.

23. The implantable device according to claim 10, wherein the piston is configured to:

perform a pump-actuated pull stroke in the rigid chamber when both the first valve and the fourth valve are in the open position and both the second valve and the third valve are in a closed position to pull fluid contents of the first expandable chamber including absorbed water from the bodily fluid into the rigid chamber through the first valve and push any fluid contents already in the rigid chamber to expel permeate from the implantable device through the fourth valve; and perform a pump-actuated push stroke in the rigid chamber when both the second valve and the third valve are in the open position and both the first valve and the fourth valve are in the closed position to pull any fluid contents of the second expandable chamber including absorbed water from the bodily fluid into the rigid chamber through the second valve and push any fluid contents already in the rigid chamber to expel permeate from the implantable device through the third valve.

* * * * *